US011471340B2

(12) United States Patent
Schnabel et al.

(10) Patent No.: US 11,471,340 B2
(45) Date of Patent: Oct. 18, 2022

(54) UNITARY STORAGE LAYER FOR DISPOSABLE ABSORBENT ARTICLES

(71) Applicant: The Procter & Gamble Company, Cincinnati, OH (US)

(72) Inventors: Martin Schnabel, Frankfurt (DE); Carola Elke Beatrice Krippner, Waldems (DE); Norbert Matthias Stelzer, Idstein (DE); Michele Mazzeo, Frankfurt (DE); Dirk Saevecke, Wiesbaen (DE)

(73) Assignee: The Procter & Gamble Company, Cincinnati, OH (US)

( * ) Notice: Subject to any disclaimer, the term of this patent is extended or adjusted under 35 U.S.C. 154(b) by 588 days.

(21) Appl. No.: 15/783,168

(22) Filed: Oct. 13, 2017

(65) Prior Publication Data
US 2018/0140480 A1 May 24, 2018

(30) Foreign Application Priority Data

Nov. 22, 2016 (EP) .................................... 16200078

(51) Int. Cl.
*A61F 13/535* (2006.01)
*A61L 15/28* (2006.01)
*A61L 15/60* (2006.01)
*A61F 13/53* (2006.01)
*A61F 13/537* (2006.01)
*A61F 13/539* (2006.01)

(52) U.S. Cl.
CPC ............ *A61F 13/535* (2013.01); *A61F 13/53* (2013.01); *A61F 13/537* (2013.01); *A61F 13/539* (2013.01); *A61L 15/28* (2013.01); *A61L 15/60* (2013.01); *A61F 2013/530051* (2013.01); *A61F 2013/5395* (2013.01); *A61F 2013/530481* (2013.01); *A61F 2013/530489* (2013.01); *A61F 2013/53966* (2013.01); *A61F 2013/53975* (2013.01)

(58) Field of Classification Search
CPC ...... A61F 13/535; A61F 13/53; A61F 13/539; A61F 13/537; A61F 2013/530481; A61F 2013/53966; A61F 2013/53975; A61F 2013/5395; A61F 2013/530489; A61F 2013/530051; A61F 2013/530547; A61L 15/60; A61L 15/28
See application file for complete search history.

(56) References Cited

U.S. PATENT DOCUMENTS

| 2,787,271 | A | 4/1957 | Catherine |
| 3,397,697 | A | 8/1968 | Rickard |
| 4,285,343 | A | 8/1981 | Mcnair |
| 4,589,876 | A | 5/1986 | Van Tilburg |
| 4,608,047 | A | 8/1986 | Mattingly |
| 4,687,478 | A | 8/1987 | Van Tillburg |
| 6,420,626 | B1 | 7/2002 | Erspamer |
| 9,399,083 | B2 | 7/2016 | Rosati |
| 10,201,462 | B2 | 2/2019 | Wright et al. |
| 2002/0007169 | A1* | 1/2002 | Graef ........................ B32B 5/26 604/378 |
| 2015/0045756 | A1* | 2/2015 | Wright .................. B01J 20/261 604/366 |

FOREIGN PATENT DOCUMENTS

| EP | 2671554 B1 | 4/2016 | |
| JP | 4785693 B2 * | 10/2011 | ........... A61F 13/494 |
| WO | 0027625 A2 | 5/2000 | |
| WO | WO03090656 A1 | 11/2003 | |
| WO | WO2005084596 A1 | 9/2005 | |
| WO | WO2000/074620 A1 | 12/2007 | |
| WO | WO2013180832 A1 | 12/2013 | |
| WO | WO2013180937 A1 | 12/2013 | |

OTHER PUBLICATIONS

EP Search Report, dated Mar. 29, 2017, 6 pages.
PCT Search Report and Written Opinion for PCT/US2017/062237, dated Feb. 28, 2018.

* cited by examiner

*Primary Examiner* — Catharine L Anderson
(74) *Attorney, Agent, or Firm* — Daniel S. Albrecht; Dara M. Kendall

(57) ABSTRACT

A unitary storage layer for an absorbent article, being formed by at least two sub-layers in which a first outermost sub-layer forms said first surface and includes cellulose pulp fibers and cross linked cellulose fibers and includes less than 5% of SAP by weight of the sub-layer, and a second sub layer which includes cellulose pulp fibers and SAP and is immediately adjacent to said first sub-layer.

13 Claims, No Drawings

UNITARY STORAGE LAYER FOR DISPOSABLE ABSORBENT ARTICLES

FIELD OF THE INVENTION

The present invention relates to a unitary storage layer which can be used in disposable absorbent articles such as sanitary napkins, panty liners, pads, baby diapers, adult incontinence articles and sweat pads. According to the present invention the storage layer is formed by a unitary layer, having first and second surfaces, which comprises two or more sub layers, typically three sub-layers.

A first sub-layer, forms the first surface of the unitary storage layer. This surface is typically intended to face the body of the user when in use. A second sub-layer is in direct contact with the surface of the first sub-layer opposite to the first surface of the storage layer. When an optional third sub-layer is present, first and third sub-layer sandwich the second. In case more sub layers are present these are sandwiched between the second and third sub-layers.

The storage layer of the present invention is designed to allow an improved liquid handling when compared with prior art solutions.

The storage layer of the invention can be used within or as an absorbent core in disposable absorbent articles sandwiching it between a topsheet and a backsheet. The storage layer of the invention may constitute the entire absorbent core or the absorbent core may be formed by the storage layer of the invention in combination with other layers as it will be described in more detail below. In particular the storage layer may be combined with one or more acquisition layer/secondary topsheet, a distribution layer or an acquisition/distribution layer which can be unitary or non unitary with the storage layer of the invention so to form an absorbent core. In a typical embodiment, the storage layers of the present invention can be incorporated as absorbent structures into absorbent articles, for example as absorbent cores or as part of their absorbent cores.

BACKGROUND OF THE INVENTION

Absorbent cores for disposable absorbent articles are commonly formed by different individual material layers which are superimposed, wherein each material layer is designed to provide specific properties. A typical structure for an absorbent core includes an acquisition layer and a storage layer, other layers can also be present such as a distribution layer, a tissue layer, a layer to provide resiliency to the products (bunching resistance), or a layer to provide a better visual impression etc. as known in the art.

The acquisition layer is typically placed on top of the body facing surface of the storage layer and has the function of rapidly acquire the fluids excreted from the body and to transfer them rapidly away from the body into the storage layer, and also to keep the storage layer separate enough from the skin so to avoid that body fluids can rewet the skin during the usage of the absorbent article. In some cases the acquisition layer has also, as secondary function, the function of distributing the fluid on a larger surface area so to provide a more efficient usage of the surface of the storage layer. In other cases this distribution function can be performed by a portion of the storage layer or by a separate layer having this specific function. This distribution layer can be placed for example below the storage layer on the surface of the storage layer which is opposite to the body facing one (garment facing surface).

In some technical documents typically relating to Feminine care articles the acquisition layer is also called "secondary topsheet". In the present application, the term "acquisition layer" is intended to be equivalent and to include also "secondary topsheets".

Each of the mentioned layers can be formed by one or more sub layers, for example the storage layers can be formed by 2 or more sub layers having the same or different functions and/or chemical composition. Also the acquisition layer can independently be formed by more sub layers, having different functions and/or chemical composition. For example, in case the acquisition layer also performs a fluid distribution function, the portion of the acquisition layer closer to the body facing surface of the absorbent element can act transferring the fluids away from the body and the portion closer to the bottom layer can act distributing the fluid along a broader surface before migrating into the storage layer.

A problem associated with using these multilayer structures as absorbent elements in absorbent articles is that fluid transfer from one layer to the other can be non optimal when the layers are separate due to the discontinuity in fluid communication. Traditionally this has been solved by using adhesives such as latexes or hot melt glues at the interface of the layers to bond the layers together, however these adhesive materials can in turn impede the fluid transfer.

In order to solve this problem "unitary" absorbent elements have been developed. The word "unitary" refers to a single structure, which, despite potential internal variations of physical and/or chemical characteristics, is provided such that it cannot be separated into individual layers without destroying the structure or damaging the layers at their interface. Absorbent structures made from a number of layers, which are joined to each other by macroscopic mechanical or adhesive means are not considered unitary since they are formed from individual layers that, albeit sometimes with difficulty, can be separated from each other again.

In other words, similarly to conventional multilayer structures, "unitary" absorbent elements are formed by several layers which can have distinct properties and/or compositions from one to the other. But, while in a "non unitary" absorbent element there is a definite boundary from one layer to the other, in a "unitary" absorbent element the various layers are somehow intermixed at the boundary region so that, instead of a definite boundary between layer it will be possible to identify a region where the different layers transition one into the other. This unitary structure is built forming the various sub-layers one on top of the other in a continuous manner, for example using air laid or wet laid deposition. Typically there is no adhesive used between the sub-layers of the of a unitary material, as this is not necessary due to the unitary construction and the combining being conducted on the layers, however in some cases adhesives and/or binders can be present although typically in a lower amount than in multilayer materials formed by separate layers.

Unitary absorbent elements and storage layers have been disclosed previously e.g. in WO03/090656A1 from Procter & Gamble, US2002/007169A1 from Weyerhaeuser and WO00/74620A1 from Buckeye.

In a unitary storage layer the fluid communication between the layers is improved, but the performance of these absorbent elements can still be further improved.

In the present invention the improvement relates to the introduction of a combination of pulp cellulose fibers and cross linked cellulose fibers in an outermost sub-layer of the unitary storage layer and precisely into the layer which receives the liquid to be absorbed first, i.e. which is intended to be positioned closer to the user's body, said sub-layer being immediately adjacent toward the garment side to a second sub-layer comprising pulp fibers and a superabsorbent polymer (SAP).

Cross linked cellulose fibers in the outermost sub-layer of the unitary storage layer provide for higher permeability of that layer and maintain a higher void volume even after the article has been wet, as opposed to a standard fluff layer which tend to collapse when wet. This layer has been surprisingly found to promote acquisition speed and to allow the underlying sub-layer comprising fluff and SAP to perform at best avoiding rewet.

SUMMARY OF THE INVENTION

The present invention relates to a unitary storage layer for an absorbent article having a first surface and a second surface opposite to said first surface, and being formed by at least two sub-layers wherein:
 a) a first outermost sub-layer forming said first surface and comprising cellulose pulp fibers and cross linked cellulose fibers and comprising less than 5% of SAP by weight of the sub-layer, and
 b) a second sub layer comprises cellulose pulp fibers and SAP and is immediately adjacent to said first sub-layer.

DETAILED DESCRIPTION OF THE INVENTION

All percentages are to be considered as weight percentages unless otherwise specified.

The unit "gsm" is intended as grams per square meter.

The term "absorbent article" is used herein in a broad sense including any article able to receive and/or absorb and/or contain and/or retain body fluids/bodily exudates such as menses, vaginal secretions, urine and faeces. Exemplary absorbent articles in the context of the present invention are disposable hygiene absorbent articles such as feminine hygiene absorbent articles such as sanitary napkins and pantyliners, pads, baby diapers, adult incontinence pads and diapers. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Absorbent articles according to the present invention include a fluid pervious topsheet, a backsheet, which may be fluid impervious and/or may be water vapour and/or gas pervious, and an absorbent core comprised there between. The term "absorbent core" in the present invention indicates the combination of all layers and materials which are sandwiched between the topsheet and the backsheet (excluding topsheet and backsheet). The storage layer of the present invention is used as a component of the absorbent core. The storage layer of the invention may constitute the entire absorbent core of the absorbent article or the absorbent core of the absorbent article can comprise other layers.

Absorbent articles according to the present invention include various types of structures, from a simple structure where the storage layer of the invention is sandwiched between a topsheet and a backsheet to more complex multi layer structures where additional layers and/or absorbent elements are present. In a typical multilayer construction, the absorbent article is made by a topsheet and a backsheet which sandwich a storage layer according to the present invention and an additional acquisition layer positioned between the topsheet and the storage layer.

In all cases, when describing the article and the absorbent structure of the present invention, it is considered that the article and the absorbent structure are in a flattened configuration where the plane of the article is the x,y plane and the z axis is perpendicular to said plane.

The term "treated pulp" is equivalent to "softener treated pulp" and to "debonder treated pulp" refers to fluff pulp treated with debonding agents which reduce the strength of hydrogen bonding between cellulose molecules.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. Topsheets may be formed by one or more layers made of the materials mentioned above, where one layer forms the outer surface of the absorbent article and one or more other layers are positioned immediately below it. The layer forming the outer surface of the article is typically a nonwoven layer or a formed film and it can be treated to be hydrophilic using surfactants or other means known to the person skilled in the art.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. In an embodiment, a microporous polyethylene or polyethylene polypropylene film can be used as backsheet. The backsheet can be formed by one or more layers and may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

Absorbent articles of the present invention may comprise side flaps. Side flaps (known to the skilled person also as "wings" or "side panels") are disclosed in the literature and are available in the marketplace. Generally, side flaps extend laterally from a central portion of the absorbent article and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties. In most cases the attachment means is similar or equal to the panty fastening means of the backsheet e.g a layer of adhesive.

The flaps serve at least two purposes. First, the flaps prevent exudates which otherwise would soil the edges of the wearer's panties from doing so. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

Side flaps can be separate elements which are attached to the sides of the main body of the absorbent article along its perimeter. Alternatively they can be formed by an extension of elements forming the main body of the article such as the topsheet, the backsheet or both. In some cases also other layers forming the absorbent article such as the absorbent core, or a secondary topsheet can extend to the side flaps.

The Storage Layer

The present invention relates to a unitary storage layer having a surface extending in the x,y plane and a thickness extending in the z direction. The storage layer of the present invention has a first surface which, when in use, is typically intended to face the body of the user (body facing surface) and an opposing second surface which during use faces toward the opposite direction (garment facing surface).

Typically the storage layer is rectangularly shaped, for ease of manufacturing. However, it may be differently shaped, for example there is frequently a wearer preference for an absorbent article which is narrower at the center than at the ends, to comfortably accommodate the legs, and obviate or minimize occurrences of bunching or wadding of the absorbent core, in this case the storage layer of the invention may be narrower at the center than at the ends. Oval shaped absorbent cores have also been proposed (e.g. WO2005/084596A1).

As mentioned above, in an absorbent article the storage layer of the invention may be the entire absorbent core, but in some embodiments additional layers will be present in particular acquisition/distribution layers. In particular an acquisition layer may be present on top of the body facing surface of the storage layer and may be unitary with it or be a discrete layer. In another embodiment two acquisition layers may be present, typically each having a reduced basis weight with respect to the embodiments where there is only one acquisition layer, wherein a first one acquisition layer is unitary with the storage layer of the invention while a second acquisition layer is a separate layer.

As known, unitary storage layers can be formed as air laid nonwoven materials, by depositing one after the other the fibers which make up the various sub-layers on a forming grid in an air laid equipment. Acquisition layers which are also unitary with the storage layers of the invention can be integrated by introducing the acquisition layer on top of the forming screen before the air laid deposition begins. This process is described in the European patent applications 14170913.9 and 14170912.1 by The Procter & Gamble Company.

The storage layer has the primary purpose to absorb and retain body fluids.

The unitary storage layer according to the present invention is formed by at least two sub-layers: a first outermost sub-layer which forms the first surface of the storage layer and which when in use is typically oriented toward the body of the user and a second sublayer which is arranged immediately adjacent on the surface of the first sub-layer which is opposite to that forming the first surface of the storage layer. Optionally and preferably a third sub-layer is present wherein the first and third sublayers sandwich the second. In case more sub-layer are present these will be sandwiched between the second and third sub-layers (so that first and third sub-layers sandwich all the other sublayers with the second sub-layer being immediately adjacent to the first).

The first sub-layer comprises pulp fibers and cross linked cellulose fibers and is substantially free of superabsorbent polymers (for substantially free it is intended that the sub-layer comprises less than 5% wt of the weight of the sub-layer of SAP). The amount of cross linked cellulose fibers can be 10% or above, or, preferably, 20% or above, or more preferably 30% or above by weight of the sub layer.

The second sub layer comprises cellulose pulp fibers and SAP and is immediately adjacent to said first sub-layer. The amount of SAP in the second sub layer can be preferably 10-80%, preferably 20-70%, more preferably 20-50% by weight of the sub-layer. Other sub layers may be present below the second sub-layer. In particular a third sub layer can be preferably present as described, this third sub layer comprising pulp fibers and optionally SAP and wherein first and third sub-layers sandwich the second sub-layer.

In addition to the required materials, the storage layer can comprise a wide variety of liquid-absorbent materials commonly used in disposable absorbent articles. Non-limiting examples of liquid-absorbent materials suitable for use in the storage layer of the absorbent element include comminuted wood pulp which is generally referred to as airfelt or pulp; creped cellulose wadding; chemically stiffened, modified, or cross-linked cellulose fibers, cotton fibers; meltblown polymers including co-form; synthetic fibers including crimped polyester fibers; capillary channel fibers; absorbent foams; absorbent sponges; synthetic staple fibers and superabsorbent polymers (SAP). Some embodiments may use, as pulp, finer fibered eucalyptus pulp, this is particularly useful in the portion of bottom layer which faces the top layer because due to its finer fibers may generate a higher and deeper penetration of the fibers from the bottom layer into the top layer.

Also non absorbent fibers may be present. For example multicomponent binder fibers can be present in the storage layer of the invention in any of the sub layers. In particular the first sub-layer may comprise up to 50%, preferably 5-50%, more preferably 5-20% by weight of the sub layer of multicomponent binder fibers.

In some embodiment the multicomponent binder fibers are bicomponent binder fibers. Bicomponent binder fibers can be formed for example by polyethylene and polypropylene, polyethylene/polyethylene terephthalate, metallocene PP with PET core, and can have any configuration known in the art such as for example core-sheath, star, fiber eccentric, fiber concentric, side by side, and mixture thereof. Multicomponent binder fibers can bind the layers without the need for additional glues, or at least reducing the need for additional glues which may impact the fluid transmission properties of the storage layer.

Other optional constituents of the storage layer according to the present invention are binders (such as latex) or glues. Optionally latex, as a dust control means, can be applied onto the outermost surfaces of the storage layer. When applied on the first surface latex is typically in an amount of from 2 to 15% by weight of first sub layer. When applied on the second surface of the storage layer latex is typically in an amount of from 2 to 15% by weight of the sub layer forming the second surface of the storage layer (which can be the second sub-layer in case of storage layer formed by 2 sub-layers, or the third sub-layer in case of a storage layer formed by more than 2 sub-layers.

Superabsorbent polymers (SAP) are known in the art and are defined herein as polymeric materials that can absorb at least 10 times their weight of an aqueous 0.9% saline solution as measured using the Centrifuge Retention Capacity test (EDANA WSP 241.2-05). Any superabsorbent polymer can be used in the present invention. Examples of superabsorbent polymers are absorbent gelling materials (AGM), and superabsorbent foam materials.

Absorbent gelling materials (AGM), are typically used in finely dispersed form, e.g. typically in particulate or fiberized form, in order to improve their absorption and retention characteristics.

AGM typically comprises water insoluble, water swellable, hydrogel forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of one or more of the fibrous layers comprised in the core, or rather localized in a more concentrated arrangement between fibrous layers so that one or more of the layers making up the core comprise a reduced amount of fibrous materials and/or are essentially made of SAP.

Other examples of SAP according to the present invention are porous or foamed superabsorbents such as those described in WO2010118272A1, WO2013180832A1 and WO2013180937A1 usable both as layers and in particulate form.

Absorbent articles according to the present invention may comprise any of the SAPs mentioned above or a mixture thereof.

The storage layer of the invention has a stratified structure which forms a so called "unitary" structure. Unitary structures in absorbent elements for absorbent articles are known in the art and described for example in are described in WO03/090656A1 from Procter & Gamble, US2002/007169A1 from Weyerhaeuser and WO00/74620A1 from Buckeye as mentioned above in the "Background of the invention" section. These documents describe absorbent cores having a unitary structure. In the present invention the unitary structure can be obtained by forming the storage layer as an airlaid material where the at least two sublayers forming it are deposited in subsequent steps on a single airlaid line.

When it is desired to add a unitary acquisition layer to the storage layer of the invention, the nonwoven material layer used for the unitary acquisition top layer can be used as a forming screen for the storage layer in the airlaid equipment so that the fibers are deposited directly on the second (garment facing) surface of the acquisition layer.

When a multilayer unitary structure is desired, the sub layers can be formed on an air laid machinery having several forming heads (in general one for each sub layer even if it could be imagined that one forming head could form two or more non adjacent layers) and wherein each forming head lays down a specific combination of materials in a given set of conditions. In this process a first forming head forms a first air laid layer, then a second forming forms a second air laid layer on top of the first layer. The process goes on until the desired series of sub-layers is obtained. Typically the deposition of an air laid layer or sub-layer the composition of the materials (fibers/agm, etc.) deposited by each forming head is constant, however it is also possible to envision embodiments of the present invention wherein the composition of the materials (fibers/agm, etc.) deposited by each forming head varies with time. This allows generating a continuous variation of composition and properties of the material along its z axis in a single layer or sub-layer. In the case where more forming heads are present it is possible to conduct also compression steps between the passage from one forming head to the other.

Alternatively also a wet laid deposition allows to form similar unitary structures as known in the art.

When the deposition of the air laid storage layer is complete the resulting material is typically compressed to compact it (e.g. via calendering). In case multicomponent binder fibers are present the material can be thermally treated at a temperature above the softening temperature of a bonding component of the multicomponent binder fibers and below the softening point of a structural component in the multicomponent binder fibers so that the binder fibers can bind also among sub-layers due to interpenetration.

As mentioned above the resulting material may be treated with additional binders on the second surface of the storage layer (such as a latex binder) to avoid dusting, the compression and thermal treatment steps can also optionally include the formation of an embossment on both surfaces of the storage layer or of the whole absorbent element. In particular it is possible include optionally an embossment on the second surface of the storage layer. Embossments might be beneficial to the wet integrity of the core, and to increase its density.

The resulting sheet of material can then be cut if necessary in the appropriate size and used as absorbent element within the absorbent core of an absorbent article or combined with an acquisition layer to form an absorbent element.

Unitary Acquisition Layer

When present a unitary acquisition layer on top of the first surface of the storage layers of the invention has the primary function of acquiring the fluids, optionally distributing said fluids over a larger surface area and then quickly transferring them to the storage layer, the storage layer has the primary function to store the absorbent fluids and prevent them from rewetting the user and optionally distributing them over a larger surface area so to ensure optimal utilization of the absorbent material.

When present a unitary acquisition layer it can be a fibrous nonwoven layer comprising fibers having an average length from 26 to 200 mm (or from 30 to 150, or from 30 to 100 mm). In some embodiments the average fiber size in dtex can be selected so to be in the range from 0.5 to 15 dtex (or from 1 to 5 dtex or from 1 to 4 dtex). The average fiber length is measured according to ASTM method D5103-07 and the average size in dtex according to the ASTM method D1577-07. The nonwoven layer forming the unitary acquisition layer can have a basis weight of from 20 to 100 gsm (or from 25 to 90 gsm) and a thickness (measured according to the method described herein) from 0.2 to 5 mm (or from 0.25 mm to 4 mm, or from 0.3 mm to 3 mm, or from 0.4 mm to 2 mm) and can be selected from needlepunched, hydroentangled, air through bonded, spunbonded, carded resin bonded, and melt blown nonwoven materials.

Hydroentangled and needlepunched nownovens are in some cases preferred because these consolidation technologies allow to obtain materials having a good z-direction compression resistance, and good capillarity even at low basis weight (thus allowing to manufacture thinner and lower cost absorbent elements).

In some preferred embodiment the nonwoven material for the unitary acquisition layer is selected in order to have a fixed height saturation at 5 cm (FHS5, measured according to the method described herein) above 40%. Nonwoven materials having this parameter in the desired range typically have good acquisition properties. Parameters that a skilled person can vary in order to tune the FHS5 are the diameter of the fibers, their cross section, their resiliency and their blend ratios.

FHS5 is dependent from the pore size or, in other words, by the size of the spaces between the fibers. Larger spaces provide a lowered FHS5 value. Fibers having a larger diameter or cross section will form layers having larger spaces between the fibers and consequently lower FHS5. As mentioned, in some embodiments a suitable range of average fiber diameter in dtex is from 0.5 to 15 dtex. A preferred range is from 1 to 5 dtex and an even more preferred one from 1 to 4 dtex.

The compaction of a layer will in general reduce the void spaces, but the resiliency of the fibers has an effect on how much compaction will in effect reduce the void spaces.

Finally fibers of different diameter can be blended in order to obtain intermediate values for FHS5.

In some embodiments the nonwoven layer forming the unitary acquisition layer comprises from 5 to 70 wt % or from 10 to 60 wt % of multicomponent binder fibers, and it is thermally bonded by them. The remaining fibers can be selected from natural, regenerated and synthetic fibers. In order to improved wettability it is preferred that at least 90% wt of the fibers (or in some embodiment 100% wt) are hydrophilic or are hydrophilically treated (e.g. with a surfactant) so to exhibit hydrophilic properties. In some embodiments also the multicomponent binder fibers can be treated so to exhibit hydrophilic properties.

Example of fibers suitable for use in the unitary acquisition layer in addition to the multicomponent binder fibers are synthetic or regenerated fibers selected from PET, polyethylene, polypropylene, nylon, rayon, polylactic acid and mixture thereof. Natural fibers may also be present such cellulosic fibers, for example cotton and/or pulp fibers.

As mentioned the unitary acquisition layer may comprise multicomponent binder fibers. Multicomponent binder fibers are fibers commonly used as binders and are known to the skilled person. Typically they comprise at least a bonding component and a structural component. The bonding component is a thermoplastic material which has a softening point which is lower than that of the structural component. Thermal bonding is achieved by heating the material at a temperature above the softening point of the bonding component and below the softening temperature of the structural component.

In some embodiments the multicomponent binder fibers are bicomponent binder fibers of the same type as described above as optional binding materials for the sub layers of the storage layer of the invention.

The thickness of the unitary acquisition layer in the absorbent element of the present invention is between 0.25 mm and 5 mm, or from 0.25 mm and 4 mm, or from 0.3 mm and 3 mm, or from 0.4 mm and 2 mm. Top layers having a very low thickness, below 0.25 mm, are not preferred because a top layer which is too thin might not be effective in preventing rewet. A very high thickness, above 5 mm, is also not preferred because it adds unnecessary bulk to the absorbent article. In general for menstrual articles a thickness between 0.25 and 1 mm is preferred while for urine management articles a thicker top layer is preferred in a range from 0.5 mm to 2 mm.

A particularly suitable material for the unitary acquisition layer is a hydroentangled fibrous structure having a basis weight between 35 grams per square meter (gsm) and 65 gsm, a machine direction (MD) bending stiffness (measured according to EDANA test method no. WSP 090.5 (Bending Length Stiffness)) of 0.2 mN·cm to 7 mN·cm, and a rewet value (measured according to EDANA test method no. WSP 070.7 (Repeated Liquid Strike-Through Time) of 0.2 g to 7.0 g. This material comprises 30% to 60%, by weight, of cellulosic fibers, 5% to 30%, by weight, of non-cellulosic fibers, and 30% to 55%, by weight, of polyolefin-based multicomponent binder fibers.

Example

Two storage layers according to the invention have been prepared and tested as follows:

|  | Comparative (gsm) | Example (gsm) |
|---|---|---|
| First sub-layer | | |
| Latex | 2.5 | 2.5 |
| Treated Cellulose Pulp | 43.8 | 26.3 |
| Cross linked cellulose | | 17.5 |
| Bicomponent PE/PP binder fiber | 8.5 | 8.5 |
| Second sub Layer | | |
| Untreated Cellulose pulp | 30 | 30 |
| SAP | 17.5 | 17.5 |
| Third sub Layer | | |
| Untreated pulp | 38.2 | 38.2 |
| SAP | 17.5 | 17.5 |
| Tissue | 17 | 17 |

Performance Evaluation

|  | Comparative | Example | |
|---|---|---|---|
| Strike-through time (fluid acquisition without blotter paper) | 11.41 s | 6.39 s | Acquisition time (5 ml saline - no filter/blotter paper) - (based on WSP 70.3), samples size 10 cm × 10 cm |
| Instant rewet (after Strike-through test without blotter paper) | 1.38 g | 0.79 g | Method: WSP 80.10<br>Rewet test with samples from strike-through test 'fluid acquisition without blotter paper'.<br>Rewet directly after completion of strike-through test with the weight placed on the sample for 10 s |

As it can be seen the replacement of a part of the cellulose pulp with cross linked cellulose pulp in the First sub-layer surprisingly reduces the strike trough time almost in half and also reduces the undesirable rewet amount in almost an half.

Test Methods

Unless otherwise specified, all tests described herein were conducted on samples conditioned at a temperature of 73° F.±4° F. (about 23° C.±2.2° C.) and a relative humidity of 50%±4% for 2 hours prior to the test.

Determination of Fluid Strike-Through

The fluid strike-through performance for the material samples of this application has been characterized with the WSP 70.3 standard test method, originally developed to characterize nonwoven coverstock. We applied the same standard method to the unitary storage layer of the invention with some changes described here below.

The method WSP 70.3 measures the strike-through time, i.e. the time taken for a known volume of liquid (simulated urine) applied to the surface of a test portion of material. When measuring nonwoven coverstock materials alone a stack of filter paper is placed below the material to suck the fluid. In the present case, testing an entire storage layer no filter paper was used. Also the sample was cut in a size of 10 cm×10 cm (while the official method requires 12.5 cm×12.5 cm).

In the test 5 ml of simulated urine (0.9% saline solution with surface tension of 70+/−2 mN/m) is discharged at a prescribed rate onto the specimen. The time taken for the entire liquid dose to penetrate the material is measured electronically.

Materials, reagents and apparatus are described in the WSP 70.3 standard test method description.

Determination of Instant Rewet (Also Called "Wetback". The Terms "Rewet" and "Wetback" are Herein Equivalent)

The instant rewet test measures the ability of a unitary storage layer to resist the transport back of a liquid which has already penetrated the test material.

For the materials described in this application the instant rewet has been measured according to the standard test method WSP 80.10, modified as described below. The standard method is designed for application to Nowoven coverstocks, in this case we have applied the modified method to the entire unitary storage layer.

Immediately after completion of the Strike trough test described above a pre-weighed pick up paper (made of filter paper) is placed on the specimen loaded with the fluid used to measure strike through and a weight is placed on top. The mass of liquid absorbed by the pick up paper is defined as rewet, calculated as the weight difference of the pre-weighted pick-up paper vs. its weight after the test.

Materials, reagents, apparatus and calculation conducted according to test method WSP 80.10. Other notable changes to the standard method are the following:

1—the samples from the strike-through test have been used (specimens size of 100 mm×100 mm loaded with 5 ml of 0.9% saline solution). Therefore WSP 80.10 procedure items 9.1-9.9 do not apply.

2—No additional liquid loading (WSP 80.10 procedure items 9.10 not conducted)

3—No pre-loading with 4 kg weight for 3 min of the sample prior to the rewet test (WSP 80.10 procedure items 9.11-9.14 do not apply)

4—The wetback test started directly after completing the strike-through test with WSP 80.10 procedure item 9.15

5—Five layers of blotter paper have been used to make up the pickup

6—The weight applied for the rewet test remained in place for 10 s (during this time wetback occurs)

Thickness

The thickness of a layer of the absorbent element structure according to the present invention, as well as of a combinations of layers, for example of an entire absorbent element structure, can be measured with any available method known to the skilled person under the selected confining pressure of 0.25±0.01 psi. For example, the INDA standard test method WSP 120.1 (05) can be used, wherein for the "Thickness testing gage" described under section 5.1, the "applied force", section 5.1.e, is set at 0.25±0.01 psi, and the "Readability", section 5.1.f, has to be 0.01 mm.

Fixed Height Saturation (FHS) at 5 cm Test Method

This test is suitable of measuring the saturation of a material at a wicking height of 5 cm providing a measure of the partially saturated suction of such a material once in contact with Saline solution.

General Apparatus Setup:

The FHS measurements setup includes: a suitable fluid delivery reservoir, has a an air tight stopcock to allow the air release during the filling of the equipment. An open-ended glass tube having an inner diameter of 10 mm extends through a port in the top of the reservoir such that there is an airtight seal between the outside of the tube and the reservoir, this allows maintaining the required zero level of the hydro head during the experiment regardless the amount of liquid in the reservoir. Reservoir is provided with delivery tube having an inlet at the bottom of the reservoir, a stopcock, with the outlet connected to the bottom of the sample holder funnel via flexible plastic tubing (e.g. Tygon®). The Fluid reservoir is firmly held in position by means of standard lab clamps and a suitable lab support. The internal diameter of the delivery tube, stopcock, and flexible plastic tubing enables fluid delivery to the sample holder funnel at a high enough flow rate to completely wet the material in less than 30 seconds. The reservoir has a capacity of approximately 1 liter. Other fluid delivery systems may be employed provided that they are able to deliver the fluid to the sample holder funnel maintaining the zero level of the hydrostatic liquid pressure at a constant height during the whole experiment.

The sample holder funnel has a bottom connector with an internal diameter of 10 mm, a measurement and a chamber where a glass frit is accommodated. The sample holder chamber has a suitable size to accommodate the sample and the confining pressure weight. The frit is sealed to the wall of the chamber. The glass frit has pore of specific size of 16-40 μm (glass frit type P 40, as defined by ISO 4793) and a thickness of 7 mm.

The confining pressure weight is a cylinder with a diameter identical to the sample size (6 cm) and a weight of 593.94 g so to apply exactly 2.06 kPa of confining pressure to the sample. The sample holder funnel is precisely held in position using a suitable lab support through a standard lab clamp. The clamp should allow an easy vertical positioning of the sample holder funnel such that the top of the glass frit can be positioned at a) the same height (+/−1 mm) of the bottom end of the open ended glass tube and b) exactly 5 cm (+/−1 mm) above the bottom end of the open ended glass tube. Alternatively two separated clamps are positioned at the abovementioned setups a and b and the sample holder funnel is alternatively moved from one to the other. During the non-usage time, the instrument is kept in proper operating conditions flooding the sample holder funnel with an excess of liquid to guarantee a proper wetting of the glass frit that should be completely below the liquid level. The sample holder funnel is also covered with an air tight cap to avoid evaporation and therefore a change in solution salinity. During storage stopcocks and are also accordingly closed to avoid evaporation as well as the open ended tube air tight sealed with a cap.

Sample Preparation

A disc of 6 cm diameter is prepared according to the above general procedure, the sample should be prepared out of the whole distribution material (e.g. a plurality of wet laid layers or folds).

Material Used:
Saline solution at a concentration of 0.9% by weight
FHS equipment
Bubble level
analytical balance with a resolution of ±0.001 g with air draft protections.
Funnel
Tweezers
Timer Experiment Setup Before Starting the Experiment:
1) the caps to the open ended tube and the sample holder funnel are removed.
2) Ensuring the stopcock is closed, the stopcock is opened to allow the air to flow out of the liquid reservoir as displaced by liquid during the refilling phase. The liquid reservoir is refilled through top end of the open-end tube with the 0.9% Saline solution with the help of suitable means such a funnel at the end of the filling the stopcock is closed.

If during all the experiments the liquid level would be close to the bottom of the open-ended tube, before running the next sample, the liquid reservoir must be refilled repeating this step number 2.
3) The sample holder funnel is removed from the lab clamp and the excess of liquid is removed pouring it away.
4) Manually holding the sample holder funnel such that the top of the glass frit lies around 10 cm below the bottom end of the open-ended tube the stop cock is carefully open until the air liquid interface in the open ended tube reaches the bottom end and a few bubble of air escape from tube. At this point the stop cock is closed.
5) The excess of liquid now present in the sample holder funnel is again disposed and the system is now ready to start the measurements.

For Each Replicate:
1) The sample holder is positioned on the clamp such that the top of the glass frit lies exactly 5 cm (+/−1 mm) above the bottom end of the open-ended tube. To ensure a reliable measure it is checked that the glass frit is perfectly horizontal with the help of a bubble level.
2) Any remaining droplet of liquid on top of the glass frit are carefully removed by means of a filter paper of any other suitable material.
3) The sample is weighed with an analytical balance with a resolution of ±0.001 g. The Weight is recorded as Dry Sample Weight (WD) to the nearest 0.001 g when the readings on the balance become constant.
4) The sample is positioned in the center of the sample holder with the help of tweezers with particular care in not altering the orientation and relative position of each of the layers of the acquisition system. It is important that the topsheet facing side of each layer is facing now downwards during the experiment in the direction of the glass frit, reproducing the liquid flow entrance direction correctly.
5) The confining weight is positioned centered on the sample
6) The stopcock is opened for 30+/−1 seconds allowing liquid to flow in the sample and then closed again.
7) The confining weight and the sample are carefully removed from the glass frit with the help of tweezers, it is important to keep track of the orientation of the sample and the relative position of the layers during the subsequent phases.
8) The sample is weighed with the analytical balance with a resolution of ±0.001 g. The Weight is recorded as 5 cm Sample Weight (W5) to the nearest 0.001 g when the readings on the balance become constant.
9) The sample is positioned back on the frit with the confining weight centered on top and the correct orientation and relative position of the layers.
10) The clamp is moved (or the sample holder funnel is positioned in another clamp) such that the top of the glass frit lies exactly at the same height (+/−1 mm) of the bottom end of the open-ended tube. To ensure a reliable measure it is checked that the glass frit is perfectly horizontal with the help of a bubble level.
11) The stopcock is opened again for 30+/−1 seconds allowing liquid to flow in the sample and then closed again.
12) The confining weight and the sample are carefully removed from the glass frit with the help of tweezers
13) The sample is weighted with the analytical balance with a resolution of ±0.001 g. The Weight is recorded as 0 cm Sample Weight (WO) to the nearest 0.001 g when the readings on the balance become constant.

The measurements of a sample are now completed and a subsequent replicate can be measured repeating the above steps. Once terminated the series of experiment around 1 cm of liquid is added on the Sample Holder funnel to completely submerge the glass frit. All the stopcocks are closed and the cap positioned according to the storage condition explained above to avoid evaporation and ensure reliability of the subsequent measurements.

Calculations.

The FHS at 5 cm (FHS5) is defined according to the following formula,

FHS5 is rounded to the nearest 0.1 and expressed as percentage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary storage layer for an absorbent article, said storage layer having a first outermost surface and a second surface opposite to said first outermost surface, and being formed by at least three sub-layers, wherein:
    a) a first sub-layer forms said first outermost surface and comprises cellulose pulp fibers and crosslinked cellulose fibers, wherein said first sub-layer further comprises less than 5% of superabsorbent polymer (SAP) by weight of said first sub-layer, and wherein said first sub-layer further comprises multicomponent binder fibers in an amount up to 50% by weight of the first sub-layer, and wherein said first sub-layer further comprises a latex-based binder disposed on said first outermost surface in an amount of from about 2% to about 15% by weight of said first sub-layer;
    b) a second sub-layer comprises cellulose pulp fibers and SAP and is immediately adjacent to said first sub-layer; and
    c) a third sub-layer comprises SAP, wherein said first and third sub-layers sandwich said second sub-layer.

2. The unitary storage layer according to claim 1, wherein said third sub-layer further comprises cellulose pulp fibers.

3. The unitary storage layer according to claim 1, wherein said crosslinked cellulose fibers comprise 10% or more by weight of said first sub-layer.

4. The unitary storage layer according to claim 1, wherein said SAP in said second sub-layer comprises about 10% to about 80% by weight of said second sub-layer.

5. The unitary storage layer according to claim 1, wherein said first sub-layer is thermally bonded by said multicomponent binder fibers.

6. The unitary storage layer according to claim 1, further comprising a latex-based binder disposed on said second surface in an amount of from about 2% to about 15% by weight of said sub-layer forming said second surface.

7. The unitary liquid storage layer according to claim 1, wherein said second sub-layer further comprises crosslinked cellulose fibers.

8. The unitary liquid storage layer according to claim 1, wherein said unitary liquid storage layer is manufactured as an airlaid material.

9. The unitary storage layer according to claim 1, having an additional unitary acquisition layer which is immediately superimposed to said first surface of said storage layer.

10. An absorbent article comprising a unitary liquid storage layer according to claim 1, said absorbent article being selected from sanitary napkins, pads, pantyliners, diapers, adult incontinence pads or diapers.

11. The unitary liquid storage layer according to claim 1 further comprising an embossment disposed on said first outermost surface.

12. The unitary liquid storage layer according to claim 1 further comprising an embossment disposed on said second surface.

13. The unitary liquid storage layer according to claim 1 further comprising embossments disposed on said first outermost surface and on said second surface.

* * * * *